US011180507B2

(12) United States Patent
Cui et al.

(10) Patent No.: US 11,180,507 B2
(45) Date of Patent: Nov. 23, 2021

(54) SYNTHESIS OF FUNCTIONALIZABLE OR FUNCTIONALIZED POLY(3,4-ETHYLENEDIOXYTHIPHENE)-BASED POLYMERS AND MONOMERS THEREFOR

(71) Applicant: University of Pittsburgh-Of the Commonwealth System of Higher Education, Pittsburgh, PA (US)

(72) Inventors: Xinyan Cui, Wexford, PA (US); Bin Cao, Allison Park, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 16/315,954

(22) PCT Filed: Jul. 10, 2017

(86) PCT No.: PCT/US2017/041286
§ 371 (c)(1),
(2) Date: Jan. 7, 2019

(87) PCT Pub. No.: WO2018/009924
PCT Pub. Date: Jan. 11, 2018

(65) Prior Publication Data
US 2020/0181163 A1 Jun. 11, 2020

Related U.S. Application Data

(60) Provisional application No. 62/359,866, filed on Jul. 8, 2016.

(51) Int. Cl.
C07D 495/04 (2006.01)
C08F 2/58 (2006.01)
C08F 28/06 (2006.01)

(52) U.S. Cl.
CPC .............. C07D 495/04 (2013.01); C08F 2/58 (2013.01); C08F 28/06 (2013.01); C08F 2400/02 (2013.01)

(58) Field of Classification Search
CPC .................................................. C07D 495/04
See application file for complete search history.

(56) References Cited

U.S. PATENT DOCUMENTS

| 7,838,688 | B2 | 11/2010 | Yeisley | |
| 2009/0008609 | A1* | 1/2009 | Yeisley | C07D 495/04 252/500 |
| 2015/0044770 | A1 | 2/2015 | Kim | |
| 2015/0337061 | A1 | 11/2015 | Yano | |

FOREIGN PATENT DOCUMENTS

WO    WO2018009924    1/2018

OTHER PUBLICATIONS

Sassi et al; Exomethylene-3,4-ethylenedioxythiopene . . . (PEDOTs); Organic letters; 2013; vol. 15; No. 14; pp. 3502-3505.*
Sassi et al (Exomethylene-3,4-ethylenedioxythiopene . . . (PEDOTs)); Organic letters; vol. 15; No. 14; pp. 3502-3505; (Year: 2013).*
McClennan; Quartetly Reviews; vol. 21, Issue 4, pp. 490-506; (Year: 1967).*
Sirringhaus, H.; Kawase, T.; Friend, R. H.; Shimoda, T.; Inbasekaran, M.; Wu, W.; Woo, E. P.; High-Resolution Inkjet Printing of All-Polymer Transistor Circuits; Science 2000, 290, issue 5499, 2123-2126.
Kim, Y. H.; Sachse, C.; Machala, M. L.; May, C.; Müller-Meskamp, L.; Leo, K.; Highly Conductive PEDOT: PSS Electrode with Optimized Solvent and Thermal Post-Treatment for ITO-Free Organic Solar Cells; Adv Fund Mater 2011, 21, 1076-1081.
De Jong, M. P.; Van Ijzendoorn, L. J.; De Voigt, M. J. A.; Stability of the interface between indium-tin-oxide and poly (3,4-ethylenedioxythiophene) / poly(styrenesulfonate) in polymer light-emitting diodes; Appl Phys Lett 2000, 77, 2255-2256.
Karagkiozaki, V.; Karagiannidis, P. G.; Gioti, M.; Kavatzikidou, P.; Georgiou, D.; Georgaraki, E.; Logothetidis, S.; Bioelectronics meets nanomedicine for cardiovascular implants: PEDOT-based nanocoatings for tissue regeneration; Biochimica et Biophysica Acta (BBA)—General Subjects 2013, issue 9, 1830, 4294-4304.
Cui, X.; Martin, D. C.; Electrochemical deposition and characterization of poly(3,4-ethylenedioxythiophene) on neural microelectrode arrays; Sensor Actuat. B Chem. 2003, 89, 92-102.
Martin, D. C.; Molecular design, synthesis, and characterization of conjugated polymers for interfacing electronic biomedical devices with living tissue; MRS Communications 2015, 5, 131-153.
Sekine, J.; Luo, S.C.; Wang, S.; Zhu, B.; Tseng, H.R.; Yu, H.-H.; Functionalized conducting polymer nanodots for enhanced cell capturing: the synergistic effect of capture agents and nanostructures; Adv Mater 2011, 23, 4788-4792.

(Continued)

*Primary Examiner* — Karuna P Reddy
(74) *Attorney, Agent, or Firm* — Bartony & Associates, LLC

(57) ABSTRACT

A method of forming a compound having the formula (I'): (I') includes the reaction: (II') in the presence of a base, wherein X is a halo atom selected from the group consisting of Cl, Br and I.

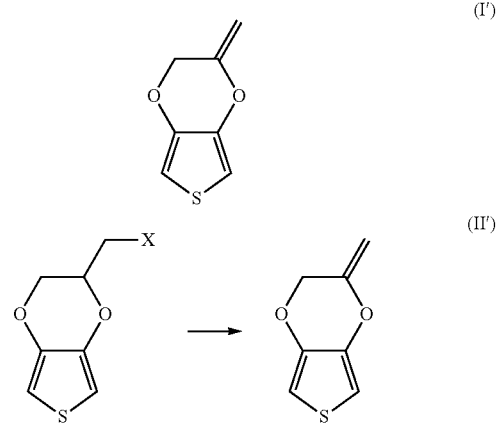

10 Claims, 7 Drawing Sheets

(56) References Cited

OTHER PUBLICATIONS

Luo, S.C.; Mohamed Ali, E.; Tansil, N. C.; Yu, H.H.; Gao, S.; Kantchev, E. A. B.; Ying, J. Y.; Poly(3,4-ethylenedioxythiophene) (PEDOT) nanobiointerfaces: thin, ultrasmooth, and funtionalized PEDOT films with in vitro and in vivo biocompatibility; Langmuir 2008, 24, 8071-8077.

Povlich, L. K.; Cho, J. C.; Leach, M. K.; Corey, J. M.; Kim, J.; Martin, D. C.; Synthesis, copolymerization and peptide-modification of carboxylic acid-functionalized 3,4-ethylenedioxythiophene (EDOTacid) for neural electrode interfaces; Biochimica et Biophysica Acta (BBA)—General Subjects 2013, 1830, 4288-4293.

Sassi, M.; Mascheroni, L.; Ruffo, R.; Salamone, M. M.; Pagani, G. A.; Mari, C. M.; D'Orazio, G.; La Ferla, B.; Beverina, L.; Exomethylene-3,4-ethylenedioxythiophene (emEDOT): A New Versatile Building Block for Functionalized Electropolymerized Poly(3,4-ethylenedioxythiophenes) (PEDOTs) Organic Letters 2013, 15, 3502.

Lu, Y.; Yang-Ping Wen.; Bao-Yang Lu, Xue-Min Duan.; Jing-Kun Xu.; Long Zhang.; Yao Huang; Electrosynthesis and characterization of poly(hydroxy-methylated-3,4-ethylenedioxythiophene) film in aqueous micellar solution and its biosensing application; Chin J Polym Sci 2012, 30, 824-836.

Calof, A. L.; Campanero, M. R.; O'Rear, J. J.; Yurchenco, P. D.; Landert, A. D.; Domain-specific activation of neuronal migration and neurite outgrowth-promoting activities of laminin; Neuron 1994, 13, 117-130.

Azemi, E.; Stauffer, W. R.; Gostock, M. S.; Lagenaur, C. F.; Cui, X. T.; Surface Immobilization of neural adhesion molecule L1 for improving the biocompatibility of chronic neutral probes in vitro characterization; Acta Biomater 2008, 4, 1208-1217.

Carter et al. The continuous flow synthesis or butane-2,3-diacetal protected building blocks using microreactors-, Organic & Biomolecular Chemistry, (2010), vol. 8, 1588-1595.

Pubmed Compound Summary for CID 102443731, '2-Methylene-2,3-dihydrothieno[3 ,4-b)-1,4-dioxin', U.S. National Library or Medicine, Dec. 26, 2015 (Dec. 26, 2015), p. 1-8 (https://pubchem.ncbi.nlm.nih.gov/compound/102443731).

\* cited by examiner

Laminin-Functionalized PEDOT-EM

Unfunctionaliazed PEDOT-EM

SYNTHESIS OF FUNCTIONALIZABLE OR FUNCTIONALIZED POLY(3,4-ETHYLENEDIOXYTHIPHENE)-BASED POLYMERS AND MONOMERS THEREFOR

CROSS-REFERENCE TO RELATED APPLICATIONS

This application is a national phase filing of PCT International Patent Application No. PCT/US2017/041286, filed Jul. 10, 2017, which claims benefit of U.S. Provisional Patent Application Ser. No. 62/359,866, filed Jul. 8, 2016, the disclosures of which are incorporated herein by reference.

GOVERNMENTAL INTEREST

This invention was made with government support under grant no. NS062019 awarded by the National Institutes of Health. The government has certain rights in this invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Since the invention at Bayer AG in late 1980s, the conducting polymer poly 3,4-ethylenedioxythiophene (PEDOT) and its derivatives have formed one of most popular categories of commercially available conducting polymeric materials for decades. Numerous applications have been achieved in a broad range of fields, from organic field-effect transistors, solar cells and light emitting diodes to nanomedicine, biosensors and bioelectronics.

In the pursuit of high efficiency and functionality of PEDOT based devices, especially in the research frontiers of biomedical field, it is highly desired to have a conducting material with readily available reactive groups for further modification and bioconjugations. However, PEDOT lacks reactive sites for direct functionalization, while the supply of commercially available 3,4-ethylenedioxythiophene (EDOT) derivatives, such as hydroxymethyl EDOT (EDOT-OH) and EDOT-acid, are limited and costly (about $300/g). The high cost has been the result of known synthesis strategies that often involve multiple reaction steps and low yield. Such challenges prevent bulk production and limit the availability and potential for widespread applications. It is very desirable to develop more convenient and cost-effective synthetic routes for large scale production of functionalized PEDOT derivatives.

SUMMARY

In one aspect, a method of forming the compound having the formula:

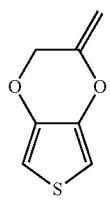

(sometimes referred to herein as exomethylene functionalized 3,4-ethylenedioxythiophene, exomethylene functionalized EDOT, or EDOT-EM) includes the reaction:

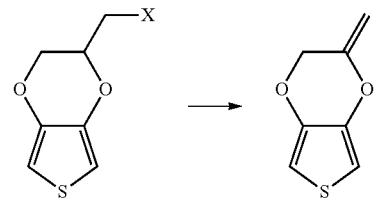

in the presence of a base, wherein X is a halo atom selected from the group consisting of Cl, Br and I. In that regard, a 2-halomethyl-2,3-dihydrothieno[3,4-b][1,4]dioxine compound reacts in the presence of a base to form EDOT-EM. In a number of embodiments, X is Cl. In a number of embodiments, the conjugate acid of the base has a pKa of at least 17. Such pKa information is readily available in published pKa tables or readily determinable using well-known procedures. The reaction may, for example, take place under conditions to limit nucleophilic addition reactions by the base. In a number of embodiments, the base is a non-nucleophilic base. In general, a non-nucleophilic base is a base which is a poor nucleophile.

In a number of embodiments, the base is selected from the group of potassium tert-butoxide, sodium tert-butoxide, tert-butyl lithium, lithium diisopropylamide, sodium hydroxide, potassium hydroxide, any other potassium alkoxide or any other sodium alkoxide. In a number of embodiments, the base is, for example, selected from the group of potassium tert-butoxide, sodium tert-butoxide, another potassium alkoxide or another sodium alkoxide The reaction may, for example, occur at a temperature in the range of approximately 0° C. to 100° C. In a number of embodiments, the reaction takes place at room temperature. In a number of embodiments, the reaction has a yield of at least 50%, at least 70%, at least 80%, at least 90%, or at least 95%.

In another aspect, a method of forming a polymer, comprising: polymerizing monomers including at least one of exomethylene functionalized 3,4-ethylenedioxythiophene or the reaction product of exomethylene functionalized 3,4-ethylenedioxythiophene and a compound including a group reactive with the exomethylene group of exomethylene functionalized 3,4-ethylenedioxythiophene via a polymerization reaction. Such monomers may be represented by the following formulas (wherein the R is the reaction product of the exomethylene group and the compound including a group reactive with the exomethylene group):

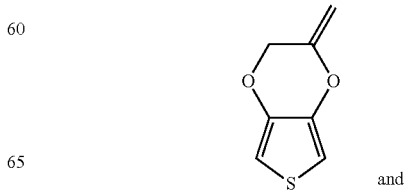

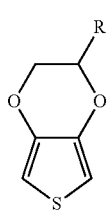

G

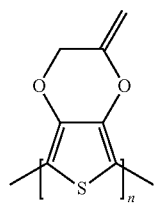

In the case that compound G is polymerized, compound G may be formed by reacting compound F with a functionalizing compound including a group reactive with an exomethylene group of compound F. In a number of embodiments, the monomers have a purity of at least 90% or at least 95% in the polymerization reaction. In a number of embodiments, the concentration of the monomers in the polymerization reaction is at least 20 mM, 30 mM, 40 mM, 50 mM or 60 mM. In a number of embodiments, electrolyte concentration is in the range of 10 mM to 1 M, or in the range of 50 mM to 200 mM. In a number of embodiments, an electrolyte concentration in the polymerization is at least 100 mM. Suitable types of electrolytes include, but are not limited to lithium, sodium, potassium, tetrabutylammonium or tetrabutylphosphonium salts with a variety of counter ions, including, for example, perchlorate, nitrate, acetate, chloride, bromide, iodide, hexafluorophosphate, tetrafluoroborate, tetraphenylborate, or polystyrene sulfonate (PSS). Other suitable electrolytes include ionic liquids such as ammonium-, pyridinium-, imidazolium-, or phosphonium-containing ionic liquids. The electrolyte may, for example, be $LiClO_4$.

Solvent systems/solvent mixtures for use in the polymerization reactions hereof include, for example mixtures of water and acetonitrile, ethanol, dimethylformamide, propylene carbonate, etc. Binary solvents (that is, mixtures of organic solvent and water) may, for example, include 5% to 95% of water. In a number of embodiments, a solvent system/solvent mixture of acetonitrile and water may be used. The acetonitrile and water may, for example, be present in a 1:1 mixture.

A potentiostatic polymerization method was used in a number of embodiments. A potential for such a reaction may, for example, be in the range of 0.6 V to 1.5 V, or in the range of 0.9 V to 1.2 V. In a number of potentiostatic polymerizations hereof, the potential may, for example, be approximately 1.1V. Electropolymerization methods such as potentiostatic or cyclic voltammetry (for example, at the same potential range as set forth above) may be used to synthesize the polymers hereof. Further, galvanostatic polymerization methods may be used with, for example, a current density in the range of 1 $\mu A/cm^2$ to 100 $\mu A/cm^2$. In a number of embodiments hereof, galvanostatic polymerization may occur at a current density of 50 $\mu A/cm^2$.

In a number of embodiments, the monomers are polymerized via electropolymerization. The method may, for example, further include functionalization of the polymer after synthesis by reacting a compound with an exomethylene group of the polymer in the case that at least some of the monomers are not functionalized prior to polymerization.

In another aspect, a method of forming a functionalized polymer includes reacting a polymer comprising the repeat group:

with at least one compound having a group reactive with an exomethylene group of the polymer. The polymer may, for example, be reacted with the at least one compound in a solution state. In a number of embodiments, the group reactive with the exomethylene group is a thiol group. The at least one compound may, for example, be a polymer. The polymer hereof (PEDOT-EM polymers) may, for example, be post-functionalized with various thiol-containing small molecules. Examples of readily available small thiol compounds include, but are not limited, to 3-mercaptopropionic acid, 3-chloro-1-propanethiol, 1-mercapto-2-propanol, 3-mercapto-1-propanol, 3-amino-1-propanethiol hydrochloride, 4-mercapto-1-butano, 6-mercaptohexanoic acid, 6-mercapto-1-hexanol, 6-mercapto-1-hexanol, 6-amino-1-hexanethiol hydrochloride, 8-mercaptooctanoic acid, 8-mercapto-1-octanol, 8-amino-1-octanethiol hydrochloride, 9-mercapto-1-nonanol, 11-mercaptoundecanoic acid, 11-mercaptoundecanamide, 11-azido-1-undecanethiol, 11-mercapto-1-undecanol, 11-amino-1-undecanethiol hydrochloride, 11-mercaptoundecylphosphonic acid, 11-mercaptoundecylphosphoric acid, 12-mercaptododecanoic acid, 1-(11-mercaptoundecyl)imidazole, (11-mercaptoundecyl)-N,N,N-trimethylammonium bromide, 11-(1H-pyrrol-1-yl)undecane-1-thiol, 6-(ferrocenyl)hexanethiol, 12-mercaptododecanoic acid NHS ester, 16-mercaptohexadecanoic acid, 16-mercaptohexadecanamide, 16-amino-1-hexadecanethiol hydrochloride, 11-mercaptoundecylhydroquinone, triethylene glycol mono-11-mercaptoundecyl ether, (11-mercaptoundecyl)tetra(ethylene glycol), 11-(ferrocenyl)undecanethiol, (11-mercaptoundecyl)hexa(ethylene glycol). The functionalized polymers may, for example, be reacted with zwitterionic amino acid cysteine for nonspecific biofouling resistance of the surface. Likewise, the polymers may be reacted with various biomolecules (for example, proteins, nucleic acids etc). The polymer may, for example, be reacted with a biomolecule such as an aptamer for use, for example, in real time neurotransmitter detection, or with one or more peptides for use, for example, in improving biocompatibility of the coated substrate with enhanced neuronal survival. Once again, the exomethylene group of the monomer may be reacted with such functionalizing compound or other functionalizing compounds reactive with the exomethylene group to create the substituent R set forth above in compound B.

The present systems, methods and compositions, along with the attributes and attendant advantages thereof, will best be appreciated and understood in view of the following detailed description taken in conjunction with the accompanying drawings.

DESCRIPTION

The present systems, methods and compositions, along with the attributes and attendant advantages thereof, will best be appreciated and understood in view of the following description taken in conjunction with any accompanying drawings.

In a number of embodiments, methods hereof provide for the synthesis of EDOT monomer having an exomethylene functional group (EDOT-EM), polymerization of such a monomer (or a functionalized derivative of such a monomer) and post-polymerization functionalization of polymers produced from such monomers.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a compound" includes a plurality of such compounds and equivalents thereof known to those skilled in the art, and so forth, and reference to "the compound" is a reference to one or more such compounds and equivalents thereof known to those skilled in the art, and so forth. Recitation of ranges of values herein are merely intended to serve as a shorthand method of referring individually to each separate value falling within the range. Unless otherwise indicated herein, and each separate value as well as intermediate ranges are incorporated into the specification as if it were individually recited herein. All methods described herein can be performed in any suitable order unless otherwise indicated herein or otherwise clearly contraindicated by the text.

Figure 1:
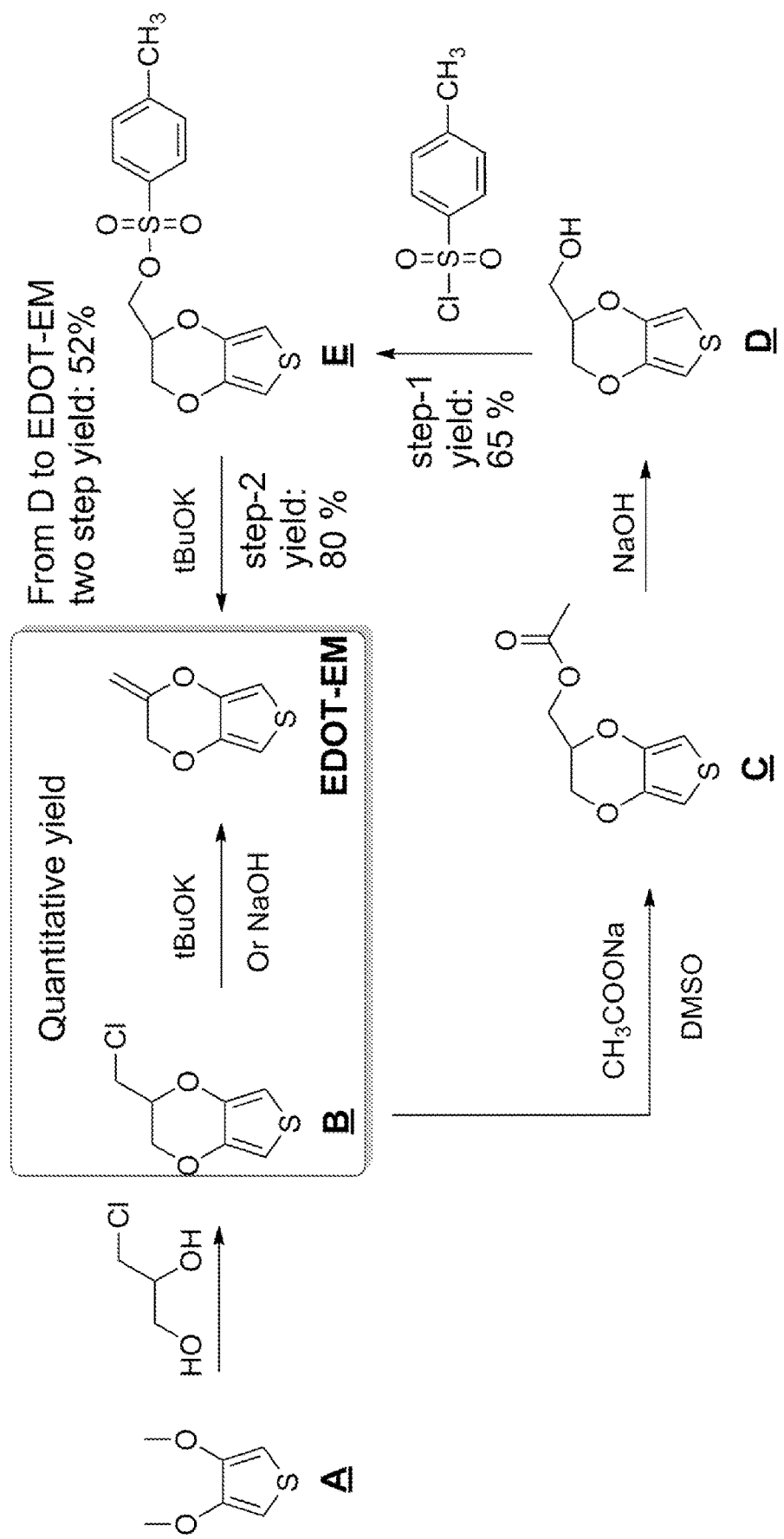
FIG. 1 illustrates synthesis of EDOT-EM in a previously published method proceeding through compounds B to E to EDOT-EM, wherein, in the synthetic method hereof, EDOT-EM is synthesized directly from representative compound B (as highlighted in the boxed scheme) with many fewer steps, faster reaction rate, quantitative conversion and extremely high yield.

The inventors hereof have discovered a simplified synthetic route for making EDOT-EM, which is a highly versatile monomer through which a wide variety of EDOT and PEDOT derivatives may be synthesized. A previously reported method for synthesizing EDOT-EM required five steps with low yields in these steps, while the present synthetic method may proceed in only a single step with a yield of ~100% at room temperature and large quantity. A comparison of the novel synthetic approach hereof and a previously reported method is illustrated in FIG. 1.

The inventors have also shown that the EDOT-EM monomer can be easily functionalized. The targeting compound EDOT-EM is a versatile intermediate that can be facilely functionalized on demand through, for example, thiol-ene click chemistry, from small molecules to macromolecular proteins. In a number of embodiments, any molecule in the "tool-box" equipped with free thiol (SH) units may be attached, via, for example, click chemistry. The monomer itself may, for example, be electropolymerized into conductive polymer and be post-functionalized with desired biomolecules such as peptides and proteins.

EDOT-OH is one of the earliest developed and most widely used EDOT intermediates. EDOT-OH was first synthesized from cyclization of diethyl 3,4-dihydroxythiophene-2,5-dicarboxylate through either a Williamson ether synthesis or Mitsunobu reaction pathway, followed by decarboxylation. However, the overall yield was relatively low. Subsequently, an alternative method was developed to synthesize EDOT-OH from 3,4-dimethoxythiophene as the starting material, through an acid catalyzed transesterification pathway as show in scheme proceeding through substituents A-E of FIG. 1. See, for example, Lu, Y.; Wen, Y.-p.; Lu, B.-y.; Duan, X.-m.; Xu, J.-k.; Zhang, L.; Huang, Y. *Chin J Polym Sci* 2012, 30, 824.

Beverina and co-workers previously carried out the synthesis of EDOT-EM with the commercially available EDOT- OH as the starting material. Sassi, M.; Mascheroni, L.; Ruffo, R.; Salamone, M. M.; Pagani, G. A.; Mari, C. M.; D'Orazio, G.; La Ferla, B.; Beverina, L. *Organic Letters* 2013, 15, 3502. As discussed above, this starting material is very expensive (possibly as a result of the 3 steps of synthesis needed from raw material and the low yield). After a tosylation of hydroxyl group on EDOT-OH followed by elimination of tosylate group, EDOT-EM was obtained with a two-step yield around 52% (see the synthetic scheme of FIG. 1). Thus, compared with the published method for the production of EDOT-EM, the present methodology requires fewer reactions, with faster reaction rate, quantitative conversion and extremely high yield. The presence of EM group in EDOT-EM provides many possibilities for derivatization by, for example, either hydro-alkoxy addition or thiol-ene click chemistry.

In the process of synthesizing EDOT-OH (compound D), during a reaction of 2-chloromethyl-2,3-dihydrothieno[3,4-b][1,4]dioxine (EDOT-MeCl, compound B) with sodium acetate to make compound C (see FIG. 1), at 120° C. in DMSO, the conversion rate to targeting compound C was lower than expected, although the reactant was completely consumed. Surprisingly, a "side product" showed even lower polarity than the reactant EDOT-MeCl (compound B). After isolation and purification, the obtained side product showed same number of carbons but one less proton compared to EDOT-MeCl, based on $^1$H and $^{13}$C nuclear magnetic resonance (NMR) spectra. From Distortionless Enhancement by Polarization Transfer (DEPT) 135 NMR spectrum, two $CH_2$ carbons were found. It was suspected that the compound could be a product from dehydrohalogenation reaction upon heating at high temperature. Soon after, detailed atomic connectivity was obtained from two-dimensional NMR heteronuclear single quantum coherence or heteronuclear single quantum correlation (HSQC) studies and heteronuclear multiple bond correlation (HMBC) studies, which confirmed that hypothesis. Without limitation to any mechanism, it is proposed that, after elimination of HCl, the product converted into an EDOT-alkene derivative EDOT-EM, and the newly-formed double bond could extend the conjugation and thus stabilize the overall molecular structure.

As shown in table 1, three different types of reagents were tested to study optimization of the reaction conditions to produce EDOT-EM at high yield. First, a non-nucleophilic strong base potassium tert-butoxide (tBuOK) was applied. Dehydrohalogenation was completed within 30 minutes at room temperature with above 95% isolation yield after washing and purification with silica gel chromatography. Second, reactions were attempted with milder bases (either sodium hydroxide or potassium hydroxide). Conversion rate was slow at room temperature but could be completed after heating at 90° C. in a sealed reaction vessel with a yield of 92%. Without limitation to any mechanism, the lower yield may be a result of a small amount of oligomerization or polymerization of EDOT-EM during heating. Finally, a weak non-nucleophilic base, diisopropylamine, was tested at both room temperature and heated condition. Reaction conversion was low and the product was not isolated. The results indicated that strong non-nucleophilic bases (pKa of conjugate acid around 17, such as sodium hydride sodium tert-butoxide and potassium tert-butoxide) are desirable for production of EDOT-EM at high yield in the present reaction schemes. Reagents with greater basicity (pKA of conjugate acid around 35-40, such as tert-butyl lithium and lithium diisopropylamide) were not tested. It is believed that in the presence of stronger bases the reaction will occur in the same manner but may be carried out at lower temperature. With moderate, non-nucleophilic bases (pKa of conjugate acid in the range of approximately 10-13 and below), reactions are slower than with stronger bases. Although sodium hydroxide and potassium hydroxide are strong nucleophiles, E2-type eliminations still proceed very well under both conditions with elevated temperature in the sealed reaction vessel.

TABLE 1

| Reagent | Reaction Time | Solvent | Temperature | Yield |
| --- | --- | --- | --- | --- |
| tBuOK | 30 min | Dry THF | RT | >95% |
| NaOH/KOH | Overnight | Methanol | 90° C. (sealed) | 92% |
| Diisopropylamine | Overnight | Methanol | 90° C. (sealed) | — |

A generalized scheme hereof for synthesis of EDOT-EM (compound F) is set forth below as

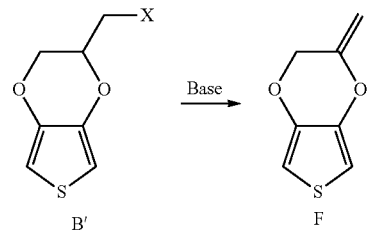

As described above, the reaction of compound B' (2-halomethyl-2,3-dihydrothieno[3,4-b][1,4]dioxine) occurs in the presence of a base and X is a halo atom selected from the group consisting of Cl, Br and I. In a number of embodiments (as, for example, described in connection with FIG. 1), X is Cl. In a number of embodiments, the conjugate acid of the base has a pKa of at least 17. Such pKa information is readily available in published pKa tables or readily determinable using well-known procedures. The reaction may, for example, take place under conditions to limit nucleophilic addition reactions by the base. In a number of embodiments, the base is a non-nucleophilic base. In general, a non-nucleophilic base is a base which is a poor nucleophile.

In a number of embodiments, the base is selected from the group of potassium tert-butoxide, sodium tert-butoxide, tert-butyl lithium, lithium diisopropylamide, sodium hydroxide, potassium hydroxide, any other potassium alkoxide or any other sodium alkoxide. The base may, for example, be selected from the group of potassium tert-butoxide, sodium tert-butoxide, another potassium alkoxide or another sodium alkoxide. The reaction may, for example, occur at a temperature in the range of approximately 0° C. to 100° C. In a number of embodiments, the reaction takes place at room temperature. In a number of embodiments, the reaction has a yield of at least 50%, at least 70%, at least 80%, at least 90%, or at least 95%.

Figure 2:
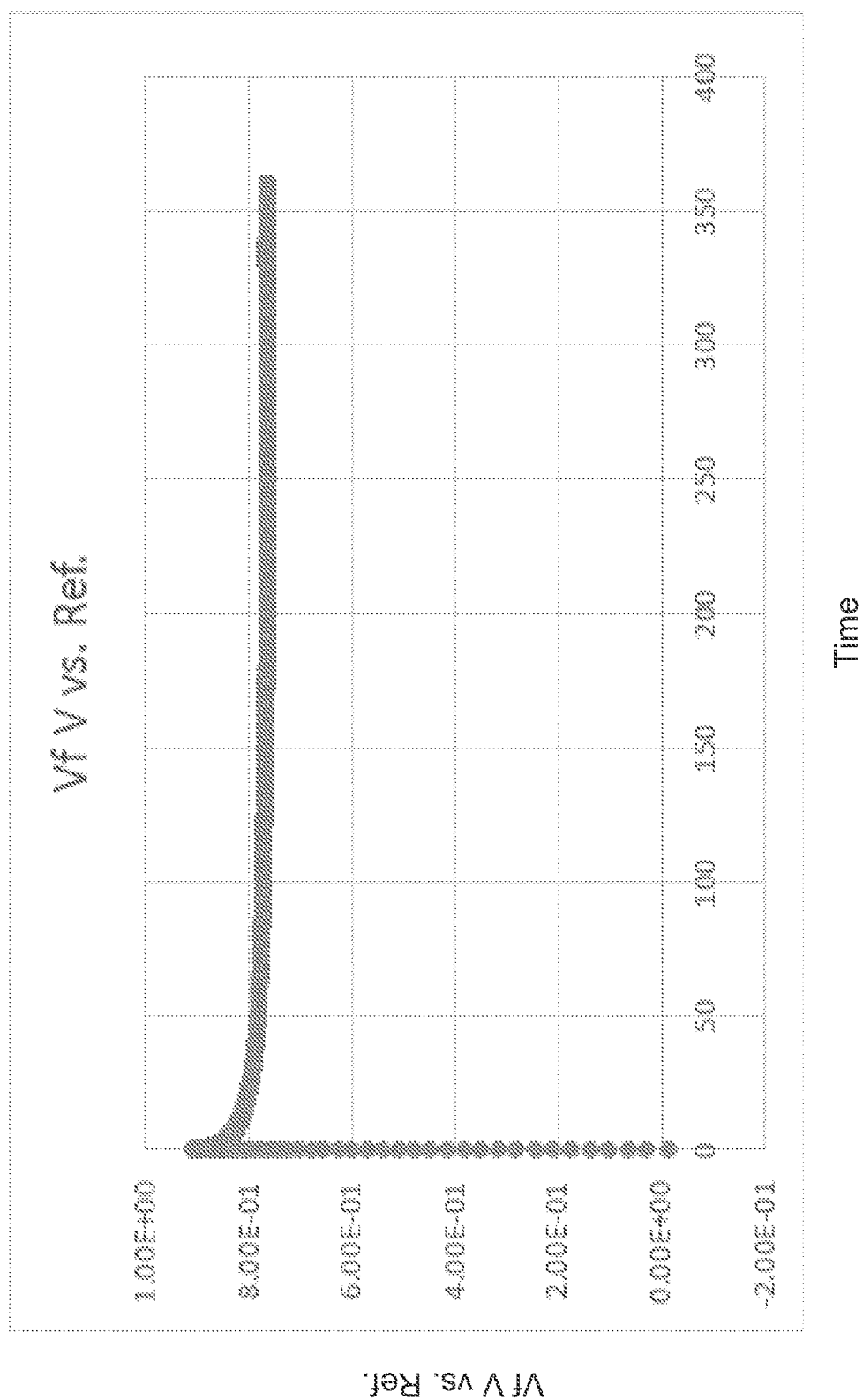
FIG. 2 illustrates a polymerization curve of EDOT-EM through a galvanostatic method.

Electro-polymerization methods were employed for their simplicity and excellent reproducibility to deposit conjugated PEDOT-EM onto different surfaces, such as indium tin oxide coated polyethylene terephthalate (ITO-PET) substrate and gold coated silicon wafers (Au—Si). The polymerization process could be monitored and processed in a precisely controlled manner by simply adjusting the potential/current and reaction time as, for example, described in Cui, X.; Martin, D. C. *Sensor Actuat. B Chem.* 2003, 89, 92, the disclosure of which is incorporated herein. Three different methods, cyclic voltammetry (CV), galvanostatic (GS), potentiostatic (PS) were tested and compared to polymerize EDOT-EM from an acetonitrile solution containing 100 mM monomer and 100 mM $LiClO_4$ as an electrolyte. The surfaces prepared from GS method showed significantly better homogeneity than those generated from CV and PS methods. As illustrated in FIG. 2, during the GS electro-polymerization process, the working potential decreased smoothly with the increase of reaction time, indicating the decrease of overall impedance and the excellent electrical conductivity of the deposited PEDOT-EM films. From a mixed solution of acetonitrile and water (1/1 v/v) containing 60 mM monomer (purity >90%) and 100 mM $LiClO_4$ as electrolyte, EDOT-EM was polymerized with a PS method at 1.1 V. In general, high purity and high concentration of monomer is preferred for successful polymerization.

Figure 3A:
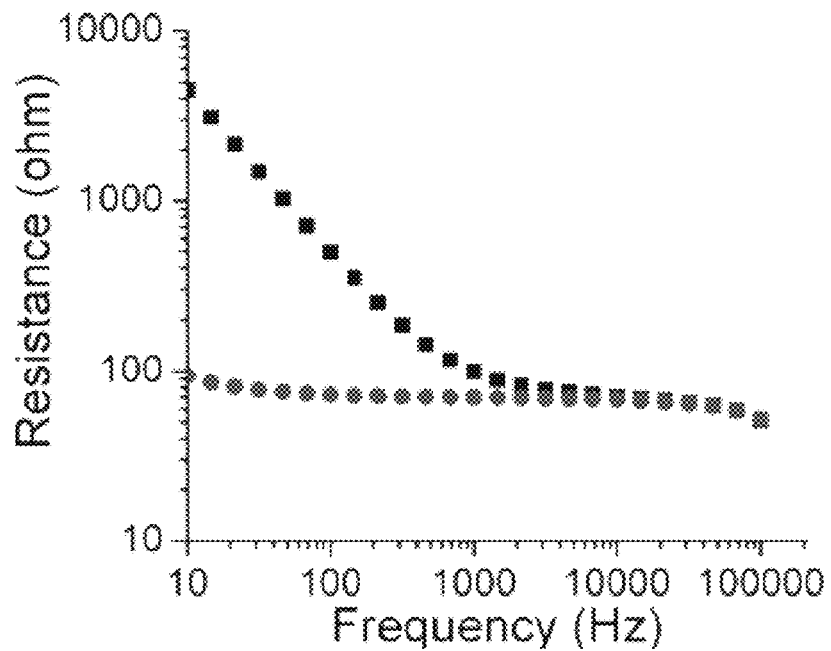
FIG. 3A illustrates a comparison of electrochemical impedance spectra (Bode plots) for PEDOT, wherein data for bare gold substrate are shown in squares and data for polymer-coated gold substrate are shown in circles.
Figure 3B:
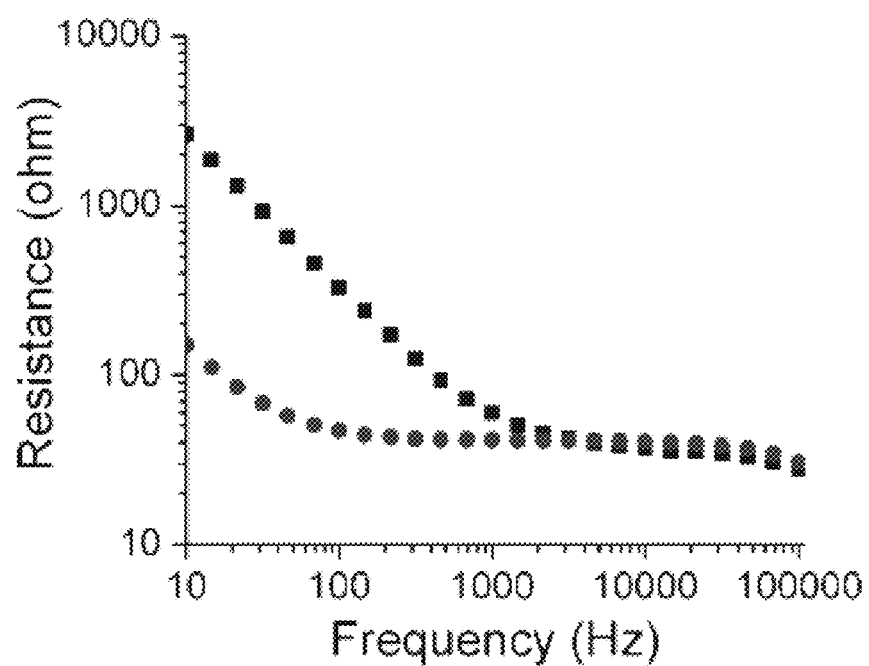
FIG. 3B illustrates a comparison of electrochemical impedance spectra (Bode plots) for PEDOT-EM samples, wherein data for bare gold substrate are shown in squares and data for polymer-coated gold substrate are shown in circles.

Both PEDOT-EM and PEDOT control films were successfully polymerized on Gold-coated silicon wafers. As shown in FIGS. 3A and 3B, electrochemical impedance spectroscopies (EIS) were recorded on both coated and uncoated substrates to test the efficiency of the polymerization as well as the quality of deposited films. PEDOT-EM film showed excellent conductivity and low impedance (FIG. 3B), similar to that of PEDOT (FIG. 3A). The impedance of the PEDOT-EM coated substrate was over one order of magnitude lower than that of the uncoated gold at a broad range of low frequencies (FIG. 3B), indicating that the interfacial impedance of the coated electrode was significantly decreased after PEDOT-EM coating, which is highly desired for many applications. In a previous report, others were unable to achieve efficient polymerization with EDOT-EM. Successful electrochemical polymerization/deposition of EDOT-EM may, for example, be the result of high polymerization rate and high molecular weight, along with many other factors, including the purity of monomer, concentration of monomer and electrolyte, type of solvent and electrolyte, method of polymerizations, etc. After screening different conditions, it is believed that the conditions used herein allow polymerization with higher molecular weight so that the reaction is more efficient to produce stable polymer films with high conductivity that are comparable to PEDOT.

Figure 4:
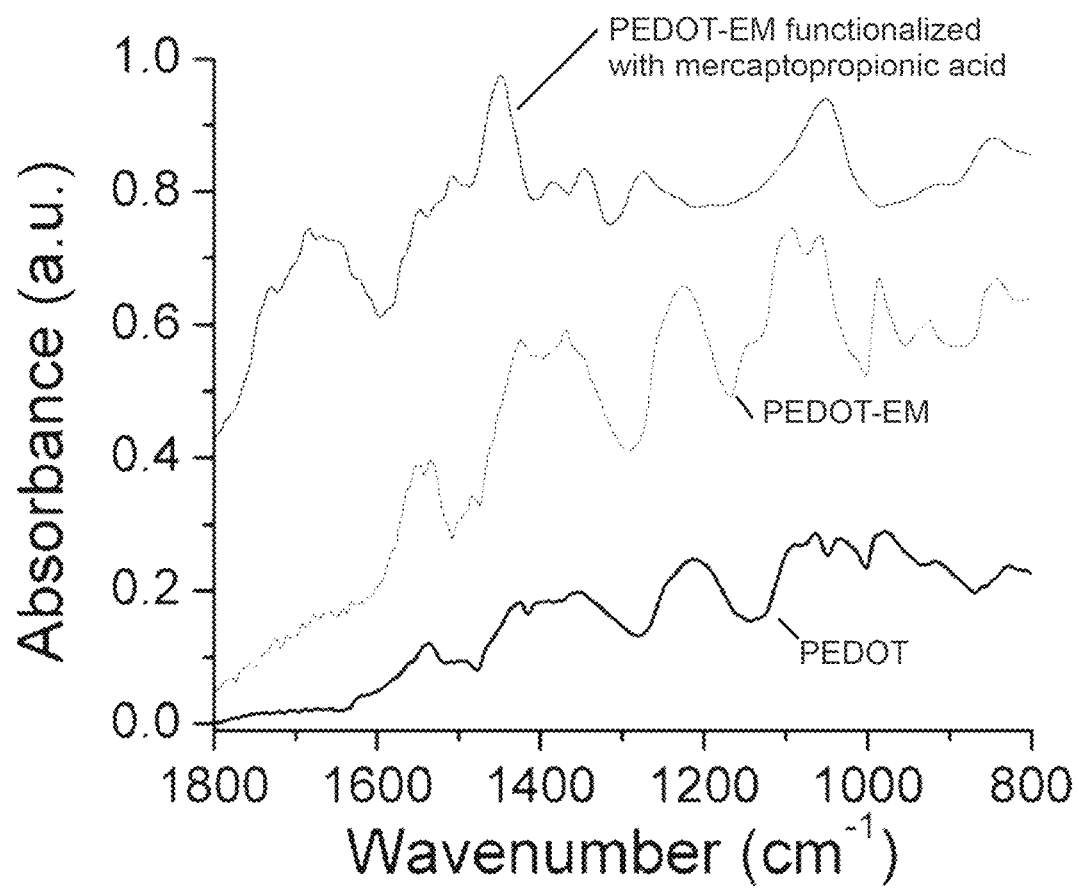
FIG. 4 illustrates FTIR spectra of PEDOT film, PEDOT-EM film, and PEDOT-EM film after functionalization with mercaptopropionic acid (MPA), wherein all films were obtained from electrochemical polymerization on Au—Si.

As described above, EDOT-EM may be functionalized with either acid catalyzed hydro-alkoxy addition or thiol-ene click chemistry. It was also demonstrated herein that one could first polymerize the EDOT-EM into PEDOT-EM and then post-functionalize the polymer on demand, with, for example, both small molecules and large proteins. In general, any molecules in the "tool-box" equipped with free thiol (SH) units could be directly attached to the polymer through the click chemistry. After the monomer has been successfully electropolymerized into conductive polymer films, the film was first post-functionalized with a small molecule, 3-mercaptopropionic acid (MPA). Attenuated total reflectance-Fourier transform infrared (ATR FTIR) spectroscopy was taken before and after functionalization of the films. PEDOT film was also tested and used as a reference. As shown in FIG. 4, The FTIR spectra of the PEDOT and PEDOT-EM slightly differ from each other. For PEDOT-EM, an addition peak at 1549 $cm^{-1}$ was attributed to EM group, which was not seen in the spectrum of PEDOT. After thiol-ene functionalization of PEDOT-EM with MPA, the appearance of the bands from carbonyl C=O stretching, between 1600 and 1800 $cm^{-1}$, confirmed the successful post-functionalization.

Figure 5A:
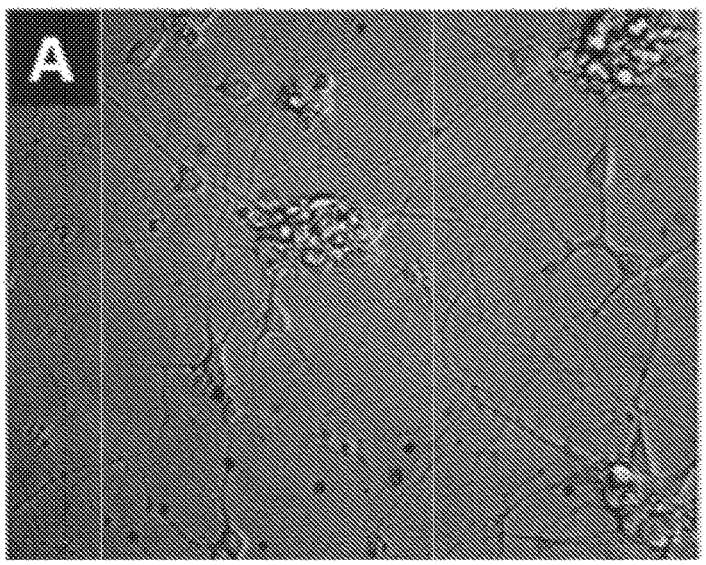
FIG. 5A illustrates a representative optical microscope image of primary neuron growth on NC-Laminin after two days in culture.
Figure 5B:
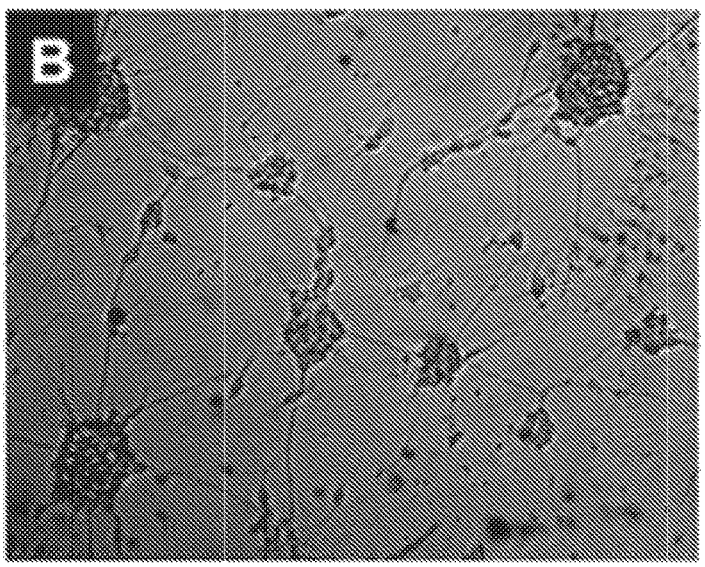
FIG. 5B illustrates a representative optical microscope image of primary neuron growth on PEDOT-EM-Laminin after two days in culture.
Figure 5C:
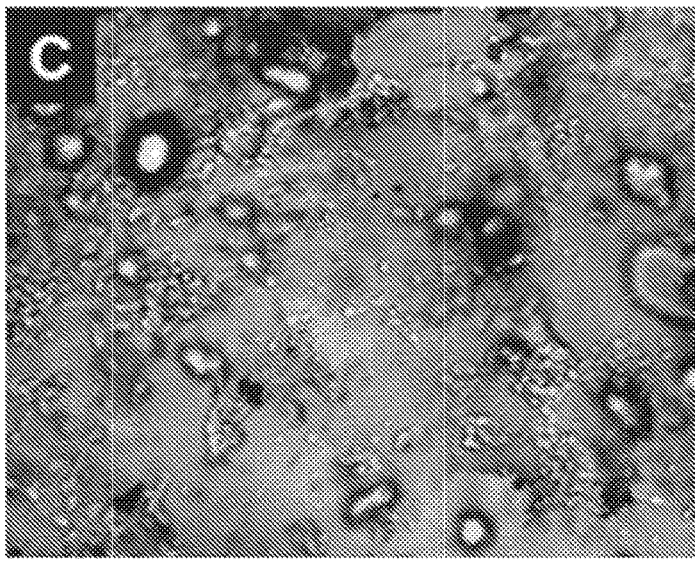
FIG. 5C illustrates a representative optical microscope image of primary neuron growth on PEDOT-Laminin after two days in culture.

For specific biosensors and bioelectrode applications, surface modification with functional proteins may be desirable. To demonstrate post-polymerization functionalization of PEDOT-EM with large biomolecules, primary neuron attachment was studied on PEDOT-EM coated substrates pretreated with laminin, a protein that is widely used to promote neuronal attachment and neurite outgrowth. In a number of studies, Laminin was applied on nitrocellulose (NC, a substrate routinely used in neuronal culture) surface, PEDOT and PEDOT-EM coated ITO-PET substrates, followed by washing in PBS three times. As shown in FIG. 5A, significant neuron attachment and growth was found on laminin coated NC surface as expected. Since PEDOT has no functional group to be conjugated with proteins, neuron growth was barely seen (FIG. 5C). Significant neuronal attachment and neurite extension were observed on the PEDOT-EM sample, suggesting that laminin was successfully bound to the PEDOT-EM surface (FIG. 5B). Although the conjugation efficiency has not been optimized, these studies demonstrate a convenient and cost-effective strategy for surface post-functionalization of conducting polymer with biomacromolecules.

Figure 6:
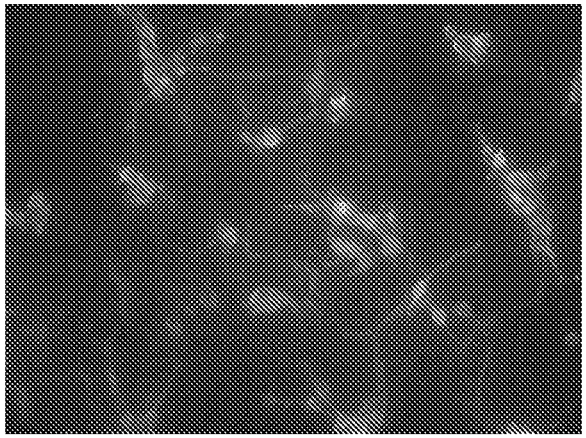
FIG. 6 illustrates photomicrographs providing a comparison of neuron cell attachment and growth between laminin-functionalized PEDOT-EM (left) and unfunctionalized or bare PEDOT-EM (right).
Figure 6:
Figure 6:
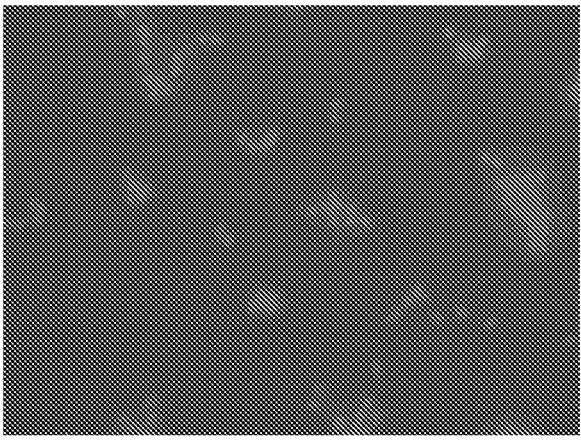
Figure 6:
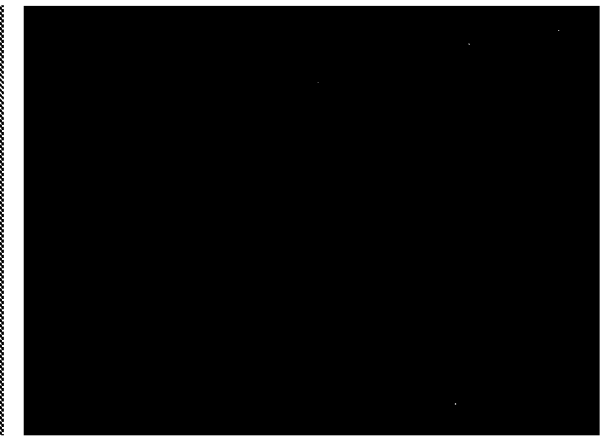

In another study, PEDOT-EM polymer film coated samples were incubated with 100 uL of 0.04 mg/ml laminin PBS solution for 1.5 hr, and then rinsed with PBS for 3 times. Primary neuron cell culture was used to validate successful post-functionalization of PEDOT-EM—with laminin protein. In these studies, direct coupling of the thiol groups on laminin is achieved via reaction with the EM on the polymer. As shown in FIG. 6, no neuron cell attachments were observed on un-functionalized bare PEDOT-EM surface. In contrast, PEDOT-EM post-functionalized with laminin showed high density neuron cell attachments as well as significant neurite growth and extension, indicating successful covalent linking of laminin protein to PEDOT-EM. In FIG. 6, high density neuron attachments were observed via blue DAPI stained nuclei (upper left photomicrograph), and neurite outgrowth and extension were observed via green, beta tubulin staining (lower left photomicrograph).

Figure 7:
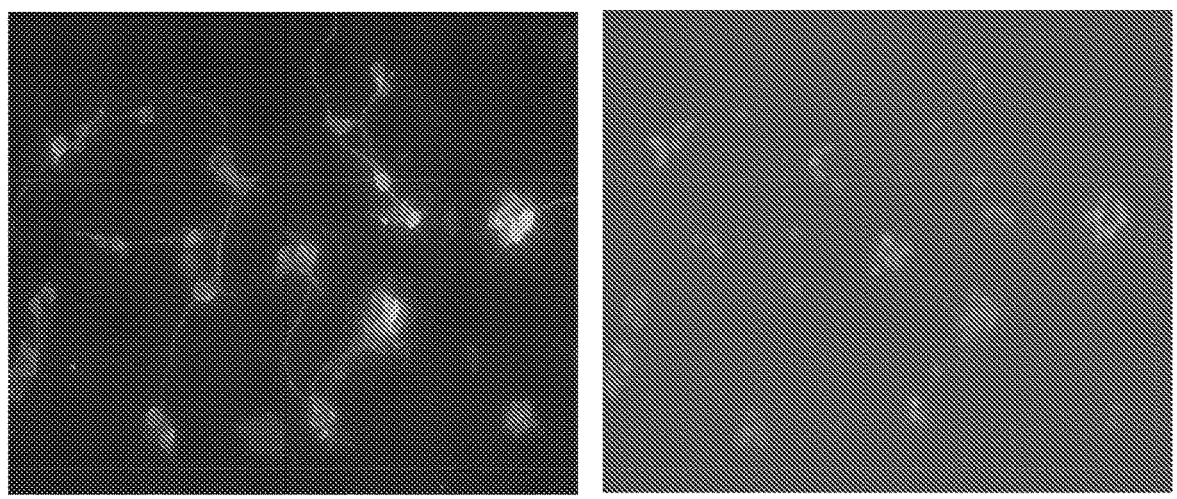
FIG. 7 illustrates photomicrograph demonstrating high density neuron cell attachment via blue DAPI stain (right photomicrograph) and significant neurite outgrowth via green beta tubulin stain (left photomicrograph) for PEDOT-EM functionalized with L1 protein via crosslinkers.

Another way to functionalize protein is to use crosslinkers that will react to the EM on one end and amine group of the protein on the other end. This methodology may, for example, be necessary when the thiol groups on the protein are critical for its function. Another advantage of this approach is that the thiol-EM reaction may sometimes require relative harsh conditions, which may result in denaturing of the protein. The use of crosslinkers may enable the use of relatively mild reaction conditions. In a number of studies, PEDOT-EM coated substrates were immersed in 1,3-propanedithiol and N-γ-maleimidobutyryl-oxysuccinimide ester (GMBS) 10 mM ethanol solution for 1 hr sequentially. Afterward L1 or L1CAM protein (a transmembrane protein) solution was incubated on the sample for another hour. All samples were rinsed with ethanol three times before use. FIG. 7 demonstrates the success of the L1 immobilization on PEDOT-EM. High density neuron attachments were observed via blue DAPI stained nuclei (right photomicrograph), and neurite outgrowth and extension were observed via green, beta tubulin staining (left photomicrograph).

Figure 8:
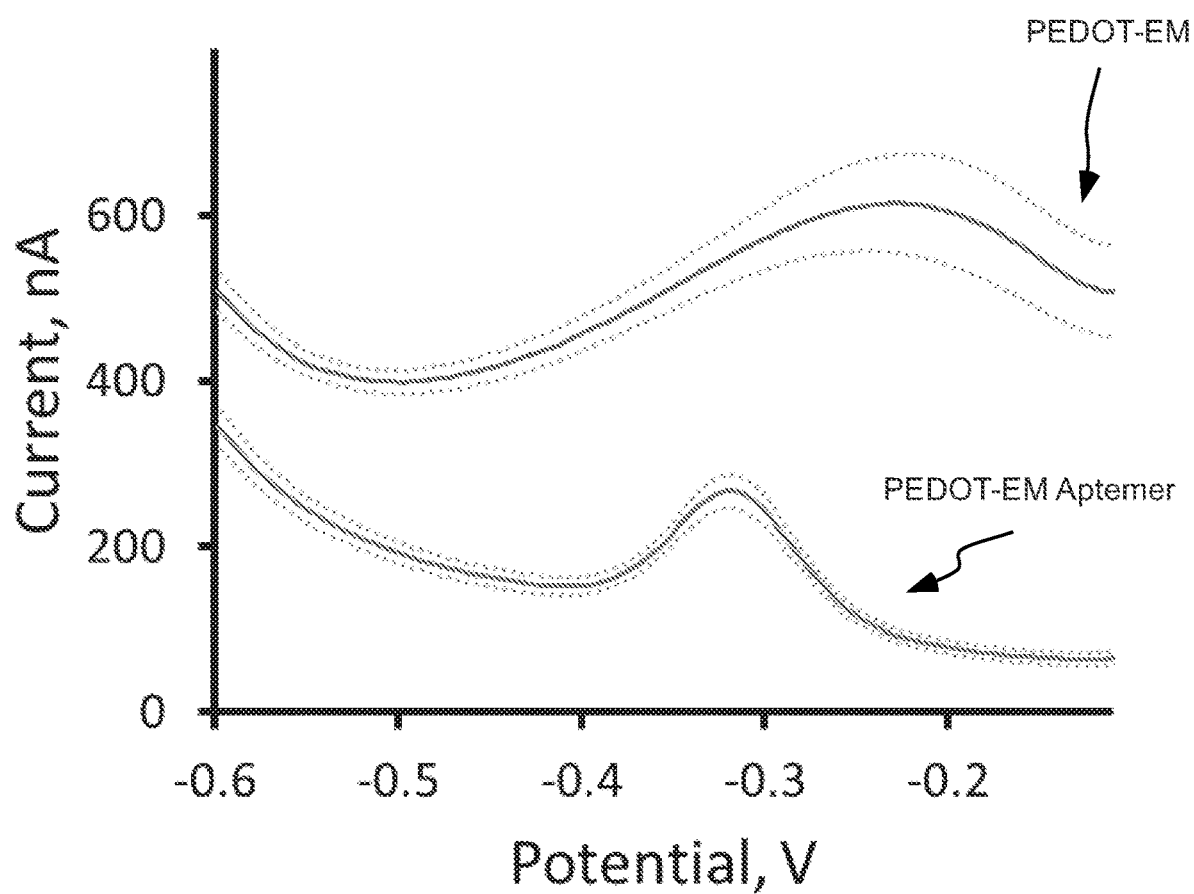
FIG. 8 illustrates a comparison of square wave voltammetry (SWV) before and after post-functionalization of PEDOT-EM with DNA aptamer based on methylene blue oxidation.

In a number of further studies, PEDOT-EM was post functionalized with DNA aptamer functionalized with methylene blue. In several such studies, PEDOT-EM coated substrates were immersed in 0.25 mg/ml aptamer PBS solution and kept at room temperature overnight. Before electro-chemical detection, all samples were rinsed with PBS for 3 times. Square wave voltammetry was used to detect successful post-functionalization of PEDOT-EM with DNA aptamer based on methylene blue oxidation. As shown in FIG. 8, before PEDOT-EM was functionalized, no methylene blue peak was observed around −0.3 V. After post-functionalization, a sharp and clear peak was observed around −0.3 V (the oxidation potential of methylene blue on the DNA aptamer), indicating the successful covalent linking of aptamer to PEDOT-EM. PEDOT-EM may, for example, be functionalized with a biomolecule such as an aptamer to develop electrochemical biosensors. Aptamers are oligonucleotide or peptide molecules that bind to a specific target molecule. The target binding to aptamer causes aptamer to change conformation which leads methylene blue to be closer or further away from the electrode surface. As a result, the change of methylene blue oxidation current can be related to target concentration.

Polymers hereof may thus be formed by polymerizing at least one monomer selected from the group of

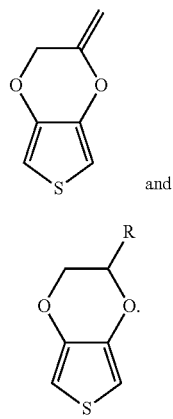

F and

G via a polymerization reaction as described herein. The monomer may, for example, be polymerized via electropolymerization as described above. If monomer F (EDOT-EM) is polymerized, the resultant polymer may be functionalized post-polymerization. Functionalization of the polymer after synthesis may, for example, occur by reacting a compound with an exomethylene group of the polymer.

In the case that compound G is polymerized, compound G may be formed by reacting compound F with a functionalizing compound including a group reactive with an exomethylene group of compound B, wherein the group R is the residue of the reaction of compound F with the functionalizing compound. In a number of embodiments, the monomer has a purity of at least 90% or at least 95% in the polymerization reaction. In a number of embodiments, the concentration of the monomer in the polymerization reaction is at least 20 mM, 30 mM, 40 mM, 50 mM or 60 mM. In a number of embodiments, electrolyte concentration is in the range of 10 mM to 1 M, or in the range of 50 mM to 200 mM. In a number of studies hereof, an electrolyte concentration in the polymerization was at least 100 mM. Electrolytes suitable for use in the polymerization reactions hereof include, but are not limited to lithium, sodium, potassium, tetrabutylammonium or tetrabutylphosphonium salts with a variety of counter ions, including, for example, perchlorate, nitrate, acetate, chloride, bromide, iodide, hexafluorophosphate, tetrafluoroborate, tetraphenylborate, or polystyrene sulfonate (PSS). Other suitable electrolytes include ionic liquids such as ammonium-, pyridinium-, imidazolium-, or phosphonium-containing ionic liquids. In a number of studies, the electrolyte was, for example, $LiClO_4$.

Solvent systems/solvent mixtures for use in the polymerization reaction hereof include, for example mixtures of water and acetonitrile, ethanol, dimethylformamide, propylene carbonate, etc. Binary solvents (that is, mixtures of organic solvent and water) may, for example, include 5% to 95% of water. In a number of studies hereof, a solvent system/solvent mixture of acetonitrile and water was used. The acetonitrile and water were, for example, present in a 1:1 mixture.

A potentiostatic polymerization method was used in a number of embodiments. A potential for such a reaction may, for example, be in the range of 0.6 V to 1.5 V, or in the range of 0.9 V to 1.2 V. In a number of potentiostatic polymerizations hereof, the potential was approximately 1.1V. Electropolymerization methods such as potentiostatic or cyclic voltammetry (for example, at the same potential range as set forth above) may be used to synthesize the polymers hereof. Further, galvanostatic polymerization methods may be used with, for example, a current density in the range of 1 $\mu A/cm^2$ to 100 $\mu A/cm^2$. In a number of embodiments hereof, galvanostatic polymerization may occur at a current density of 50 $\mu A/cm^2$.

As described above, the exomethylene group of EDOT-EM or PEDOT-EM may be reacted with a compound having a group reactive with an exomethylene group of the polymer. The reaction may, for example, occur in a solution state. In a number of embodiments, the group reactive with the exomethylene group is a thiol group. The at least one compound may, for example, be small molecule or a polymer. Examples of readily available small thiol compounds for reaction with the exomethylene group include, but are not limited to, 3-mercaptopropionic acid, 3-chloro-1-propanethiol, 1-mercapto-2-propanol, 3-mercapto-1-propanol, 3-amino-1-propanethiol hydrochloride, 4-mercapto-1-butano, 6-mercaptohexanoic acid, 6-mercapto-1-hexanol, 6-mercapto-1-hexanol, 6-amino-1-hexanethiol hydrochloride, 8-mercaptooctanoic acid, 8-mercapto-1-octanol, 8-amino-1-octanethiol hydrochloride, 9-mercapto-1-nonanol, 11-mercaptoundecanoic acid, 11-mercaptoundecanamide, 11-Azido-1-undecanethiol, 11-mercapto-1-undecanol, 11-Amino-1-undecanethiol hydrochloride, 11-mercaptoundecylphosphonic acid, 11-mercaptoundecylphosphoric acid, 12-mercaptododecanoic acid, 1-(11-mercaptoundecyl)imidazole, (11-mercaptoundecyl)-N,N,N-trimethylammonium bromide, 11-(1H-pyrrol-1-yl)undecane-1-thiol, 6-(ferrocenyl)hexanethiol, 12-mercaptododecanoic acid NHS ester, 16-mercaptohexadecanoic acid, 16-mercaptohexadecanamide, 16-amino-1-hexadecanethiol hydrochloride, 11-mercaptoundecylhydroquinone, triethylene glycol mono-11-mercaptoundecyl ether, (11-mercaptoundecyl)tetra(ethylene glycol), 11-(ferrocenyl)undecanethiol, (11-mercaptoundecyl)hexa(ethylene glycol). The exomethyl group(s) may alternatively, for example, be reacted with zwitterionic amino acid cysteine for non-specific biofouling resistance of the surface. Likewise, the monomers or polymers hereof may be reacted with various biomolecules (for example, proteins, nucleic acids etc). The monomers or polymers may, for example, be reacted with a biomolecule such as an aptamer for use, for example, in real time neurotransmitter detection, or with one or more peptides for use, for example, in improving biocompatibility of the coated substrate with enhanced neuronal survival.

Once again, the exomethylene group of the monomer may be reacted with such functionalizing compound or other functionalizing compounds reactive with the exomethylene group to create the substituent R set forth above in compound B. In forming functionalized EDOT polymers, the EDOT-EM monomer may be functionalized (as described above) prior to polymerization. In addition to thiol-ene chemistry, other reactions may occur, as known in the chemical arts, with the exomethylene group either prior to polymerization or after polymerization in forming a functionalized EDOT monomer or polymer.

The foregoing description and any accompanying or incorporated drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method of forming a monomer:

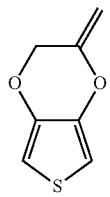

comprising, the reaction:

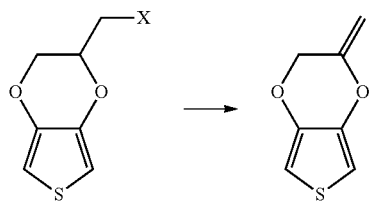

in the presence of a base which is potassium tert-butoxide in a single reaction vessel at room temperature and a reaction time of 30 minutes to achieve a yield of at least 95% with quantitative conversion, wherein X is a halo atom selected from the group consisting of Cl, Br and I.

2. The method of claim 1 wherein the reaction takes place under conditions to limit nucleophilic addition reactions by the base.

3. The method of claim 1 wherein the reaction yield is approximately 100%.

4. The method of claim 1 wherein X is Cl.

5. A method of forming a polymer, comprising:
forming exomethylene functionalized 3,4-ethylenedioxythiophene monomer having the formula:

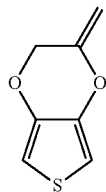

via the reaction:

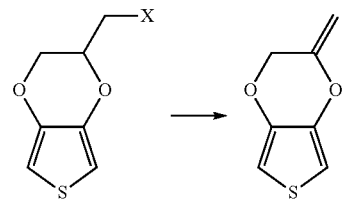

in the presence of a base which is potassium tert-butoxide in a single reaction vessel at room temperature and a reaction time of 30 minutes to achieve a yield of at least 95% with quantitative conversion, wherein X is a halo atom selected from the group consisting of Cl, Br and I; and polymerizing monomers comprising at least one of the exomethylene functionalized 3,4-ethylenedioxythiophene monomer or a reaction product of the exomethylene functionalized 3,4-ethylenedioxythiophene monomer and a compound including a group reactive with the exomethylene group of the exomethylene functionalized 3,4-ethylenedioxythiophene monomer via a polymerization reaction, wherein the monomers have a purity of at least 95% in the polymerization reaction.

6. The method claim 5 wherein the polymerization reaction is an electropolymerization reaction and the method further comprises functionalization of the polymer after synthesis by reacting with a compound including a group reactive with the exomethylene group of the exomethylene functionalized 3,4-ethylenedioxythiophene.

7. The method of claim 5 wherein the monomers have a concentration of at least 20 mM in the polymerization reaction.

8. The method of claim 5 wherein the group reactive with the exomethylene group is a thiol group.

9. The method of claim 5 wherein the compound including the group reactive with the exomethylene group is selected from the group consisting of 3-mercaptopropionic acid, 3-Chloro-1-propanethiol, 1-mercapto-2-propanol, 3-mercapto-1-propanol, 3-amino-1-propanethiol hydrochloride, 4-mercapto-1-butano, 6-mercaptohexanoic acid, 6-mercapto-1-hexanol, 6-mercapto-1-hexanol, 6-amino-1-hexanethiol hydrochloride, 8-mercaptooctanoic acid, 8-mercapto-1-octanol, 8-amino-1-octanethiol hydrochloride, 9-mercapto-1-nonanol, 11-mercaptoundecanoic acid, 11-mercaptoundecanamide, 11-azido-1-undecanethiol, 11-mercapto-1-undecanol, 11-amino-1-undecanethiol hydrochloride, 11-mercaptoundecylphosphonic acid, 11-mercaptoundecylphosphoric acid, 12-mercaptododecanoic acid, 1-(11-mercaptoundecyl)imidazole, (11-mercaptoundecyl)-N,N,N-trimethylammonium bromide, 11-(1H-pyrrol-1-yl)undecane-1-thiol, 6-(ferrocenyl)hexanethiol, 12-mercaptododecanoic acid NHS ester, 16-mercaptohexadecanoic acid, 16-mercaptohexadecanamide, 16-amino-1-hexadecanethiol hydrochloride, 11-mercaptoundecyl hydroquinone, triethylene glycol mono-11-mercaptoundecyl ether, (11-mercaptoundecyl)tetra(ethylene glycol), 11-(ferrocenyl)undecanethiol, (11-mercaptoundecyl)hexa(ethylene glycol), or a biomolecule.

10. The method of claim 9 wherein the biomolecule is a zwitterionic amino acid cysteine, a peptide, a protein, or a nucleic acid.

* * * * *